(12) United States Patent
Krakauer

(10) Patent No.: US 6,406,862 B1
(45) Date of Patent: Jun. 18, 2002

(54) DIP-STICK ASSAY FOR C-REACTIVE PROTEIN

(75) Inventor: Teresa Krakauer, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/413,361

(22) Filed: Oct. 6, 1999

Related U.S. Application Data

(60) Provisional application No. 60/103,196, filed on Oct. 6, 1998, and provisional application No. 60/118,362, filed on Feb. 3, 1999.

(51) Int. Cl.[7] ................................................ G01N 33/53
(52) U.S. Cl. ............................ 435/7.1; 435/4; 435/7.6; 435/7.92; 435/805; 436/513; 436/518; 530/380; 530/388.1; 530/389.1
(58) Field of Search ............................. 435/4, 7.1, 7.5, 435/7.6, 7.92, 7.93, 7.94, 805; 436/513, 518; 530/380, 388.1, 389.1

(56) References Cited

U.S. PATENT DOCUMENTS

| 4,632,901 A | * | 12/1986 | Valkris et al. | 435/5 |
| 4,642,285 A | * | 2/1987 | Halbert et al. | 435/7 |
| 5,177,021 A | * | 1/1993 | Knodo | 436/518 |
| 5,272,258 A | * | 12/1993 | Siegel et al. | 530/388.25 |
| 5,447,837 A | * | 9/1995 | Urnovitz | 435/5 |

OTHER PUBLICATIONS

Mandall et al. C reactive protein and its relation to cardio-vascular risk factors; a population based cross sectional study. British Medical Journal. vol. 312 (1996) pp. 1061–1065.*

* cited by examiner

Primary Examiner—Jeffrey Stucker
Assistant Examiner—Ulrike Winkler
(74) Attorney, Agent, or Firm—Elizabeth Arwine; Charles H. Harris

(57) ABSTRACT

A C-reactive protein concentration level test and kit for on-site determination of C-reactive protein levels in biological samples is disclosed.

11 Claims, 1 Drawing Sheet

DIP-STICK ASSAY FOR C-REACTIVE PROTEIN

This application claims benefit of priority from earlier filed Provisional application Ser. No. 60/118,362 filed on Feb. 3, 1999, now abandoned, and Provisional application Ser. No. 60/103,196 filed on Oct. 6, 1998, now abandoned.

BACKGROUND OF THE INVENTION

The present invention relates to a rapid, semi-quantitative test method for the determination of levels of C-reactive protein in biological fluids.

C-reactive protein (CRP) is a prototypic acute phase protein in humans that increases rapidly in concentration as a result of tissue injury, inflammation or infection. The normal range of serum CRP is 0.08–3 milligram (mg) per liter (l). However, CRP levels can increase between 100–1000-fold during an inflammatory response. Elevated serum levels of CRP are seen 6–12 hours (h) after an inflammatory stimulus, and maximum levels are reached within 48–72 h. Generally, CRP levels will return to normal 55–10 days after remission of inflammation. Because the accumulation of CRP in serum closely parallels the course of inflammation and tissue injury, CRP has been used as a diagnostic tool to detect inflammation and to monitor the clinical course of various diseases. For example, CRP levels are found to exceed 50 mg/l in rheumatoid arthritis, systemic lupus erythematosus (SLE), ulcerative colitis, Crohn's disease, acute pancreatitis, cardiac infarction, septicemia, bacterial meningitis, and pneumonia.

The standard test for CRP in the clinic in the United States is by rate nephelometry using the Beckman Array system (Beckman, Fullerton, Calif.) with a detection limit of 10 mg/l. Other methods including turbidimetry (Multistat, Instrument Laboratory, Lexington, MA) and fluorescence polarization immunoassay are also used in European countries. Commercial ELISA kits for measurement of low levels of CRP are also available but are not used clinically because the procedures are lengthy require special instruments/reader, and trained technicians to perform the assay. The choice of method will be determined by a number of factors. For large hospitals and diagnostic laboratories, automated, quantitative determination of CRP can be performed with specialized instruments by highly trained technicians. Typically, physicians' ordered CRP tests are performed in a centralized diagnostic laboratory and turnaround time of a day or so is normal. Latex agglutination and Nycocard (Nycomed Pharma AS, Oslo, Norway), methods that have been developed in recent years for CRP measurements that can be performed in the physician's office, are faster, although not necessarily more accurate alternatives.

Therefore, there is a need for a rapid, sensitive, and accurate assay for the measurement of CRP levels in biological fluids such that the assay can be conducted in a physicians office or on site and does not require costly equipment or highly skilled personnel to operate the instruments.

SUMMARY OF THE INVENTION

The present invention satisfies the need discussed above. The present invention relates to an accurate, fast, dip-stick method for assaying and quantitating the amount of CRP in a biological sample. The assay has particular application to serum samples and can be conducted at the location where the patient is found and does not require sophisticated equipment.

The assay is a multiple tube procedure using a solid support coated with polyclonal antibodies to CRP in which the solution of the final tube will result in a color change of the solid support where presence of intense color will indicate high levels of CRP in the serum and faint color will indicate low levels of CRP in the serum. The assay reagents, pipettes/dropper, and test tubes may be provided in the form of a kit.

BRIEF DESCRIPTION OF THE DRAWINGS

These and other features, aspects, and advantages of the present invention will become better understood with reference to the following description and appended claims, and accompanying drawings where:

DETAILED DESCRIPTION OF THE INVENTION

Figure 1:
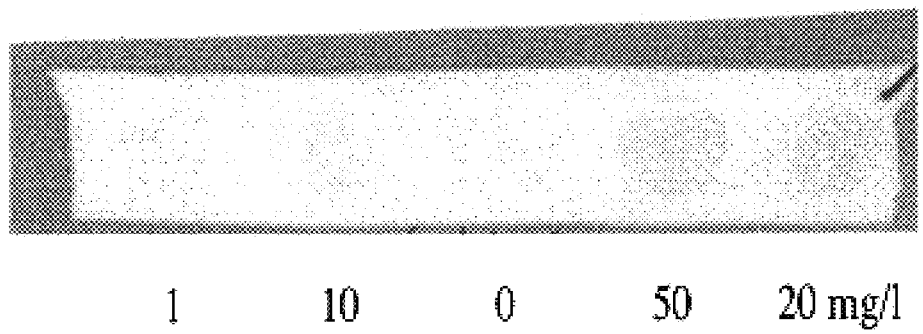
FIG. 1 represents a test strip showing a gradation of color with increasing intensity corresponding to 0, 10, 20, and 50 mg/l of CRP.

To assay CRP in a patient's biological sample such as serum, urine, cell culture supernatant for example, the invention comprises the steps of:

(i) binding an antibody against CRP to a solid support;

(ii) incubating said solid support in the presence of the sample to be analyzed under conditions where antibody-antigen complexes form;

(iii) incubating said support with an anti-CRP antibody conjugated to a detectable moeity which produces a signal;

(vi) detecting said signal wherein said signal is proportional to the amount of CRP in said sample;and (v) comparing the signal in said sample to a standard.

The solid support can be a any phase used in performing immunoassays, including dipsticks, membranes, absorptive pads, beads, microtiter wells, test tubes, and the like. Preferred are test devices which may be conveniently used by the testing personnel or the patient for self-testing, having minimal or no previous training. Such preferred test devices include dipsticks, membrane assay systems as described in U.S. Pat. No. 4,632,901. The preparation and use of such conventional test systems is well described in the patent, medical, and scientific literature. If a stick is used, the anti-CRP antibody is bound to one end of the stick such that the end with the antibody can be dipped into the solutions as described below for the detection of CRP. Alternatively, the samples can be applied onto the antibody-coated dipstick or membrane by pipette or dropper or the like.

The antibody against CRP can be of any isotype, such as IgA, IgG or IgM, Fab fragments, or the like. The antibody may be a monoclonal or polyclonal and produced by methods as generaly described in Harlow and Lane, *Antibodies, A Laboratory Manual*, Cold Spring Harbor Laboratory, 1988, incorporated herein by reference. Rabbit anti-human CRP antibody can detect human, rabbit and rat CRP, and anti-dog CRP antibody can be used for detecting dog CRP. The antibody can be applied to the solid support by direct or indirect means. Indirect bonding allows maximum exposure of the CRP binding sites to the assay solutions since the sites are not themselves used for binding to the support. Preferably, polyclonal antibodies are used since polyclonal antibodies can recognize different epitopes of C-reactive protein thereby enhancing the sensitivity of the assay. Polyclonal antibodies for use in the assay can be rabbit anti-CRP from DAKO, Carpinteria, Calif. for example.

The solid support is preferably be non-specifically blocked after binding the C-reactive protein antibodies to the solid support. Non-specific blocking of surrounding areas can be with whole or derivatized bovine serum albumin, or albumin from other animals, whole animal serum, casein, non-fat milk, and the like.

The sample is applied onto the solid support with bound C-reactive protein-specific antibody such that the C-reactive protein will be bound to the solid support through said antibodies. Excess and unbound components of the sample are removed and the solid support is preferably washed so the antibody-antigen complexes are retained on the solid support. The solid support may be washed with a washing solution which may contain a detergent such as Tween-20, Tween-80 or sodium dodecyl sulfate.

After the C-reactive protein has been allowed to bind to the solid support, a second antibody which reacts with C-reactive protein is applied. The second antibody may be labeled, preferably with a visible label. The labels may be soluble or particulate and may include dyed immunoglobulin binding substances, simple dyes or dye polymers, dyed latex beads, dye-containing liposomes, dyed cells or organisms, or metallic, organic, inorganic, or dye solids. The labels may be bound to the C-reactive antibodies by a variety of means that are well known in the art. In some embodiments of the present invention, the labels may be enzymes that can be coupled to a signal producing system. Examples of visible labels include alkaline phosphatase, beta-galactosidase, horseradish peroxidase, and biotin. Many enzyme-chromogen or enzyme-substrate-chromogen combinations are known and used for enzyme-linked assays.

Simultaneously with the sample, corresponding steps may be carried out with a known amount or amounts of CRP and such a step can be the standard for the assay.

The solid support is washed again to remove unbound labeled antibody and the labeled antibody is visualized and quantitated. The accumulation of label will generally be assessed visually. This visual detection may allow for detection of different colors, e.g., red color, yellow color, brown color, or green color, depending on label used. Accumulated label may also be detected by optical detection devices such as reflectance analyzers, video image analyzers and the like. The visible intensity of accumulated label could correlate with the concentration of C-reactive protein in the sample. The correlation between the visible intensity of accumulated label and the amount of C-reactive protein may be made by comparison of the visible intensity to a set of reference standards. Preferably, the standards have been assayed in the same way as the unknown sample, and more preferably alongside the sample, either on the same or on a different solid support. The concentration of standards to be used can range from about 1 mg of CRP per liter of solution, up to about 50 mg of CRP per liter of solution. Preferably, several different concentrations of CRP are used so that quantitating the unknown by comparison of intensity of color is more accurate. An intensity of color similar to 10 mg/l of CRP is considered negative, as compared with an intensity of color similar to 50 mg/l.

This assay can be used to detect an infection which correlates with an increase of CRP levels at or above 40 mg/l. In severe bacterial infection, CRP levels as high as 170 mg/l can be detected. Normal range is about 0.08–3 mg/l [(Clin. Chem. 43, 52 (1997)] Additionally, the assay can be used to monitor the CRP levels of a patient during therapy since CRP levels should decrease if the therapy is useful. As evident to a person with ordinary skill in the art, it may be necessary to undergo one or more serial dilutions of the patients sample such that the level of CRP in the patients sample can be compared to one of the set standards. The patient CRP measurement is then corrected for the dilution factor.

Although each of the steps can be carried out in the same vessel, such as a test tube, if it is cleaned and washed after each of the steps, a fast and convenient on-site assay is best performed according to the invention by using three separate vessels for each of the steps, one for the sample, one for washing, and one for developing the detectable label.

An aspect of the present invention which results in significant advantages over prior assays conducted under laboratory conditions, is the amount of sample used. In the previous assays, a volume of 200 ul is required to run the assay. The present invention requires about 5 ul of sample, which is easily aquired. The use of disposable and yet accurate pipettes for such volume is responsible for the invention process being more accurate and less expensive and time consuming than prior processes.

All the materials and reagents required for assaying CRP according to the present invention can be assembled together in a kit. This generally will comprise one or more solutions containing a known concentration of CRP, a washing solution, a solution of a chromogen which changes color or shade by the action of the enzyme directly or indirectly through action on a substrate, an anti-CRP antibody conjugated to a label such that it could be detected, pipettes for the transfer of said solutions, test tubes for said solutions, and a solid support, in particular adapted to be inserted into the test tubes, carrying on the surface thereof a polyclonal antibody to CRP. The kit may also contain one or more solid support having an anti-CRP antibody for use in assaying one or more samples simultaneously or individually, and the necessary reagent required to develop the label. It is also preferable that the CRP used for standards be provided so that it could be assayed fresh along with the unknown sample. Such kits will comprise distinct containers for each individual reagent.

In the above test kit, the reagents may be supplied from storage bottles or one or more of the test tubes may be prefilled with the reagents or controls.

The components of the kit may also be provided in dried or lyophilized forms. When reagents or components are provided as a dried from, reconstitution generally is by the addition of a suitable solvent. It is envisioned that the solvent also may be provided in another container means.

The kits of the present invention also will typically include a means for containing the reagents such as vials or tubes in close confinement for commercial sale such as, e.g. injection or blow-molded plastic containers into which the desired vials are retained.

The following example is included to demonstrate an embodiment of the invention. It should be appreciated by those of skill in the art that in light of the present disclosure, many changes can be made in the specific embodiment disclosed and still obtain a like or similar result without departing from the spirit and scope of the invention.

The following MATERIALS AND METHODS were used in the examples that follow.

Preparation of Dip-stick

Nitrocellulose paper (Biorad, Calif.) was cut into strips 8–9 mm wide and variable lengths (40–75 mm) depending on the number of samples to be applied to the strip. Antibodies directed against human CRP (DAKO, Calif.) were diluted 2-fold with Hanks balanced salts solution (HBSS) and applied to strips at 7 mm intervals, and incubated at 37° C. for 2 h. Strips were blocked with HBSS with 2% bovine serum albumin (BSA) and 0.05% Tween 20 for 1 hour. At this point, strips can be stored dry in a sealed plastic bag at 4° C. for later use.

CRP Assay

CRP standards (Accurate, Calif.), 0.5–50 mg/liter, were applied to the strips on the spots that had been precoated with polyclonal anti-CRP. The spots were then allowed to dry for 10 min. A blank of 10% fetal calf serum (FCS) in RPMI was included as a negative control. Strips were washed in 15 ml test tubes containing 14.5 ml of HBSS with 0.05% Tween 20 (wash buffer) two time sequentially. Strips were then placed in a 15 ml test tube containing 14.5 ml of horseradish peroxidase-conjugated anti-hCRP in 1% BSA for 10 min. with occasional shaking. The strips were then washed with wash buffer two times as above. The bound CRP was then detected by placing strips in a test tube of TMB (3,3',5,5'-tetramethyl benzidine) (Kierkegaard and Perry Laboratories, Gaithersburg, Md.) solution. Upon the appearance of a faint green color on the strips (usually<1 minute), strips were then placed in a tray of water (60 ml) and rinsed. Color spots can be visually graded or photographs can be taken for permanent record.

EXAMPLE 1

The intensity of color spots with 1, 10, 20, 50 mg/l were compared with that of a true blank consisting of 10% FCS immediately or within 30 min after the last wash. Blank spots had a greenish tint similar to background with nothing coated. Samples containing 1 mg/l had a greenish tint as the blank. A gradation of green color of increasing intensity was observed with 10, 20, 50 mg/l (FIG. 1). Spots with 50 mg/l CRP had intense green color that lasted for hours (7–18 hours), much longer that the spots with 10 mg/l of CRP. Spots with 10 mg/l tend to fade away in 2–3 hours after reaction with TMB. Based on these results, a threshold of 10 mg/l can be set as a negative. An unknown CRP sample from a patient with a 67 mg/l of CRP was detected as a positive in this test.

Based on the standards at various concentrations and using a cut-off level of 10 ug/ml, the sensitivity and specificity of this test were 97% and 90% respectively.

In conclusion, this rapid, easy to perform assay for CRP requiring no special instruments makes this an ideal on-the-spot test for CRP. The high sensitivity and specificity of this test can guide the physician in the clinical diagnosis of infection and inflammatory diseases.

What is claimed is:

1. A method for detecting tissue injury, inflammation or infection in a subject comprising measuring levels of C-reactive protein in a biological sample of said subject, comprising (i) binding an antibody against CRP to a solid support chosen from the group consisting of dip-stick and membrane;
    (ii) incubating said solid support in the presence of the sample to be analyzed under conditions where antibody-antigen complexes form;
    (iii) incubating said support with an anti-CRP antibody conjugated to a detectable moeity which produces a signal;
    (vi) visually detecting said signal wherein said signal is proportional to the amount of CRP in said sample; and
    (v) comparing the signal in said sample to a standard wherein a level equal to or below 10 mg/l is considered negative, and a level above 10 mg/l is considered indicative of tissue injury, infection or inflammation in said subject.

2. The method of claim 1 wherein said biological sample is serum.

3. The method of claim 1 wherein the standard is assayed simultaneously along with the biological sample.

4. The method of claim 1 wherein said standards range from about 10 mg of CRP per liter of solution to about 100 mg of CRP per liter of solution.

5. The method of claim 1 wherein said detection is by use of a chromogen.

6. The method according to claim 5 wherein said chromogen, is 3,3'5,5'-tetramethylbenzidine or its derivative.

7. The assay according to claim 1 wherein said assay is performed at room temperature.

8. The assay according to claim 1 wherein said biological sample is 5 microliters.

9. The method according to claim 1 wherein said method is performed at room temperature.

10. A test kit for visual detection of C-reactive protein wherein detection of a level equal to or below 10 mg/l is considered negative, and a level above 10 mg/l is considered indicative of tissue injury, infection or inflammation in said subject, said kit comprising:

one or more solutions containing a known concentration of CRP to serve as a standard;
    a solution of a anti-CRP antibody bound to an enzyme;
    a chromogen which changes color or shade by the action of the enzyme;
    a solid support chosen from the group consisting of dip-stick and membrane carrying on the surface thereof an antibody to C-reactive protein.

11. A test kit of claim 10 wherein said kit further comprises test tubes for said solutions.

* * * * *